US011660065B2

(12) United States Patent
Tahmasebi Maraghoosh et al.

(10) Patent No.: US 11,660,065 B2
(45) Date of Patent: May 30, 2023

(54) METHOD AND SYSTEM FOR MULTI-MODAL TISSUE CLASSIFICATION (71) Applicant: KONINKLIJKE PHILIPS N.V., Eindhoven (NL)

(72) Inventors: Amir Mohammad Tahmasebi Maraghoosh, Ridgefield, CT (US); Shyam Bharat, Cambridge, MA (US); Christopher Stephen Hall, Kirkland, NY (US); Jochen Kruecker, Washington, DC (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 1411 days.

(21) Appl. No.: 14/891,768

(22) PCT Filed: Jun. 19, 2014

(86) PCT No.: PCT/IB2014/062422
§ 371 (c)(1),
(2) Date: Nov. 17, 2015

(87) PCT Pub. No.: WO2014/207627
PCT Pub. Date: Dec. 31, 2014

(65) Prior Publication Data
US 2016/0098621 A1 Apr. 7, 2016

Related U.S. Application Data
(60) Provisional application No. 61/839,424, filed on Jun. 26, 2013.

(51) Int. Cl.
G06K 9/62 (2022.01)
A61B 8/08 (2006.01)
(Continued)

(52) U.S. Cl.
CPC .............. *A61B 8/085* (2013.01); *A61B 5/055* (2013.01); *A61B 8/5223* (2013.01);
(Continued)

(58) Field of Classification Search
CPC ...... A61B 8/085; A61B 8/5223; A61B 8/5261
See application file for complete search history.

(56) References Cited

U.S. PATENT DOCUMENTS

| | | | |
|---|---|---|---|
| 5,754,676 A | 5/1998 | Komiya et al. | |
| 6,317,617 B1 | 11/2001 | Gilhuijs et al. | |

(Continued)

FOREIGN PATENT DOCUMENTS

| | | |
|---|---|---|
| CN | 1973297 A | 5/2007 |
| CN | 103083046 A | 5/2013 |

(Continued)

OTHER PUBLICATIONS

Chiu, B. et al.., "Characterization of carotid plaques on 3-dimensional ultrasound imaging by registration with multicontrast magnetic resonance imaging", Journal of Ultrasound in Medicine, Oct. 2, 2012, pp. 1567-1580.

(Continued)

*Primary Examiner* — Rochelle D Turchen
(74) *Attorney, Agent, or Firm* — Sherry Austin (57) ABSTRACT

A method for multi-modal tissue classification of an anatomical tissue involves a generation of a tissue classification volume (40) of the anatomical tissue derived from a spatial registration and an image extraction of one or more MRI features of the anatomical tissue and one or more ultrasound image features of the anatomical tissue. The method further involves a classification of each voxel of the tissue classification volume (40) as one of a plurality of tissue types including a healthy tissue voxel and an unhealthy tissue voxel.

15 Claims, 4 Drawing Sheets

(51) Int. Cl.
　　*A61B 5/055*　　　(2006.01)
　　*G06T 7/00*　　　(2017.01)
　　*G06T 7/30*　　　(2017.01)
　　*G06F 18/24*　　　(2023.01)
　　*G06T 15/08*　　　(2011.01)

(52) U.S. Cl.
　　CPC ............ *A61B 8/5261* (2013.01); *G06F 18/24* (2023.01); *G06T 7/0012* (2013.01); *G06T 7/30* (2017.01); *G06T 15/08* (2013.01); *G06T 2207/10088* (2013.01); *G06T 2207/10132* (2013.01); *G06T 2207/30024* (2013.01); *G06T 2207/30081* (2013.01)

(56) References Cited

U.S. PATENT DOCUMENTS

| | | | |
|---|---|---|---|
| 7,636,420 | B2 | 12/2009 | Spies et al. |
| 7,640,051 | B2 | 12/2009 | Krishnan et al. |
| 2005/0075566 | A1 | 4/2005 | Satoh |
| 2007/0167705 | A1 | 7/2007 | Chiang et al. |
| 2008/0037851 | A1 | 2/2008 | Takayama |
| 2008/0132782 | A1 | 6/2008 | Rueckmann et al. |
| 2010/0286517 | A1 | 11/2010 | Kamen et al. |
| 2011/0137148 | A1 | 6/2011 | Khizhnichenko |
| 2011/0178389 | A1 | 7/2011 | Kumar et al. |
| 2012/0083696 | A1 | 4/2012 | Kitamura |
| 2012/0155734 | A1* | 6/2012 | Barratt ............... G06T 7/35 382/131 |
| 2012/0189176 | A1 | 7/2012 | Giger et al. |
| 2013/0035594 | A1 | 2/2013 | Eda |
| 2013/0046168 | A1 | 2/2013 | Sui |
| 2013/0116542 | A1 | 5/2013 | Gross |
| 2015/0003706 | A1* | 1/2015 | Eftestol ............... G06T 7/0012 382/131 |

FOREIGN PATENT DOCUMENTS

| | | |
|---|---|---|
| JP | 2005111258 A | 4/2005 |
| JP | 2007524461 A | 8/2007 |
| JP | 2010057649 A | 3/2010 |

OTHER PUBLICATIONS

Kruecker, J. et al., "Fusion of real-time trans-rectal ultrasound with pre-acquired MRI for multi-modality prostate imaging", Proceedings of SPIE, SPIE—International Society for Optical Engineering, US, vol. 6509, Mar. 21, 2007, p. 650912/1.

Chappelow, J. et al., "Improving supervised classification accuracy using non-rigid multimodal image registration: detecting prostate cancer", Proceedings of SPIE, vol. 6915, Mar. 6, 2008, p. 6915OV.

Nakano, S. et al., "Impact of real-time virtual sonography, a coordinated sonography and MRI system that uses an image fusion technique, on the sonographic evaluation of MRI-detected lesions of the breast in second-look sonography", Breast Cancer Research and Treatment, Kluwer Academic Publishers, BO, vol. 134, No. 3, Jul. 24, 2012, pp. 1179-1188.

Sonn, G.A et al., "Targeted biopsy in the detection of prostate cancer using an office based magnetic resonance ultrasound fusion device", J. Urol. Jan. 2013, 189(1):86-91.

Marks, L. et al., "Ultrasound-MRI Fusion for Targeted Diagnosis of Prostate Cancer: Use of Artemis Device to Evaluate Organ-Confined Lesions", Center for Advanced Surgical and Interventional Technology, Apr. 17, 2013, Health & Medicine News.

* cited by examiner

METHOD AND SYSTEM FOR MULTI-MODAL TISSUE CLASSIFICATION

CROSS-REFERENCE TO PRIOR APPLICATIONS

This application is the U.S. National Phase application under 35 U.S.C. § 371 of International Application Ser. No. PCT/IB2014/062422, filed on Jun. 19, 2014, which claims the benefit of U.S. Application Ser. No. 61/839,424 filed on Jun. 26, 2013. These applications are hereby incorporated by reference herein.

The present invention generally relates to an imaging of anatomical tissues. The present invention specifically relates to a utilization of multiple imaging modalities for screening, detecting and treating unhealthy (e.g., cancerous) anatomical tissues.

Prostate cancer is one of the most common organ malignancies among American men. Historically, a "gold standard" for prostate cancer diagnosis is a histopathologic analysis of biopsy tissue samples whereby elevated prostate specific antigen ("PSA") levels and results of digital rectal exam ("DRE") tests are considered as the screening. However, a PSA test yields low specificity and sensitivity, and detection by palpation through DRE is limited to relatively large and superficial lesions.

In ultrasound ("US") imaging, tissue classification based on acoustic parameters (e.g., attenuation and backscattered coefficients) extracted from radio frequency ("RF") echo signals has been studied since the early 1970$s$. More particularly, texture features extracted from B-mode US images and spectral features extracted from calibrated average spectrum of RF echo signals have been used along with numerous classification approaches for tissue typing as healthy or cancerous. However, while US imaging provides high temporal resolution imaging of the anatomical tissue of interest, accuracy of ultrasound-based cancer detection techniques has proven to be limited due to poor signal-to-noise ratio and low spatial resolution.

More particularly, transrectal ultrasound ("TRUS") is sometimes used as an alternative step in the screening process for prostate cancer. However, approximately 40% of the peripheral zone hypoechoic lesions have proven to be malignant. Therefore, a clinical value of TRUS is limited to a biopsy guidance tool.

Recently, there has been significant interest in using magnetic resonance imaging ("MRI") for diagnosis of prostate cancer due to its high anatomical resolution. However, a diagnostic value of anatomical T2-weighted ("T2W") MRI in distinguishing prostate cancer from benign prostate lesions is limited. For example, it has been shown that the accuracy, sensitivity and positive predictive values of prostate cancer detection using MRI for tumor foci greater than 1.0 cm in diameter are 79.8%, 85.3%, and 92.6%, respectively. Moreover, the accuracy, sensitivity and positive predictive values of prostate cancer detection using MRI decreases to 24.2%, 26.2%, and 75.9%, respectively, for tumor foci smaller than 1.0 cm.

However, a combination of anatomic, biologic, metabolic and functional dynamic information offered by multi-parametric MRI has been shown to improve prostate cancer detection accuracy. A few of the common functional MR imaging techniques that have been utilized for prostate cancer detection are dynamic contrast enhanced MR imaging ("DCE"), proton MR spectroscopic imaging ("MRSI"), and diffusion-weighted MR imaging ("DWI"). More particularly, DCE visualizes tissue vascularity, MRSI provides metabolic information and DWI shows the Brownian motion of extracellular water molecules.

Importantly, a standard of care in prostate cancer therapy is moving from a 'whole gland' approach (e.g., radical prostatectomy, whole gland radiation and brachytherapy) to more focused and localized treatment paradigms designed to only treat specific cancerous regions within the prostate. A step in this direction is the ability to accurately identify these localized cancerous regions. However, in spite of the improved capabilities of multi-parametric MRI, it is still inherently difficult for observers to accurately identify cancerous regions in a consistent manner. Furthermore, in ultrasound images, the B-mode US image processing pipeline suppresses potential tissue signatures that may assist in differentiating cancerous tissue from normal tissue.

In general, the present invention recognizes that an automated decision support system or computer-aided diagnosis that includes different algorithms to perform image registration, image segmentation, image feature extraction, image delineation and tissue classification on multi-modality images may provide a systematic and objective approach to fuse information from different types of images. Specifically, the present invention is premised on combining tissue information extracted from spatially registered MRI images (e.g., T1W, T2W, a DWI, a DCE and MRSI) and US images (e.g., a B-mode image and a RF echo image) in order to form a vector of unique image features for each voxel of the registered images. Such a multi-modal (US-RF-MRI) vector of features combines the advantages of the multi-modalities to achieve higher accuracy, sensitivity and specificity in detecting prostate cancer.

One form of the present invention is a system for multi-modal tissue classification of an anatomical tissue that employs one or more MRI systems, one or more ultrasound systems and a workstation. In operation, the MRI system(s) generate one or more MRI features of the anatomical tissue and the ultrasound system(s) generate one or more ultrasound image features of the anatomical tissue. The workstation generates a tissue classification volume of the anatomical tissue derived from a spatial registration and an image extraction of the MRI feature(s) and the ultrasound image feature(s) of the anatomical tissue. The workstation further classifies each voxel of the tissue classification volume as one of a plurality of tissue types including a healthy tissue voxel and an unhealthy tissue voxel.

A second form of the present invention is a workstation for multi-modal tissue classification of an anatomical tissue employing an image registrator, a feature extractor and a tissue classifier. In operation, the image registrator and the feature extractor generate a tissue classification volume of the anatomical tissue derived from a spatial registration and an image extraction of one or more MRI features of the anatomical tissue and one or more ultrasound image features of the anatomical tissue. The tissue classifier classifies each voxel of the tissue classification volume as one of a plurality of tissue types including a healthy tissue voxel and an unhealthy tissue voxel.

A third form of the present invention is a method for multi-modal tissue classification of an anatomical tissue involving a generation of a tissue classification volume of the anatomical tissue derived from a spatial registration and an image extraction of one or more MRI features of the anatomical tissue and one or more ultrasound image features of the anatomical tissue. The method further involves a classification of each voxel of the tissue classification volume as one of a plurality of tissue types including a healthy tissue voxel and an unhealthy tissue voxel.

The foregoing forms and other forms of the present invention as well as various features and advantages of the present invention will become further apparent from the following detailed description of various embodiments of the present invention read in conjunction with the accompanying drawings. The detailed description and drawings are merely illustrative of the present invention rather than limiting, the scope of the present invention being defined by the appended claims and equivalents thereof.

Figure 1:
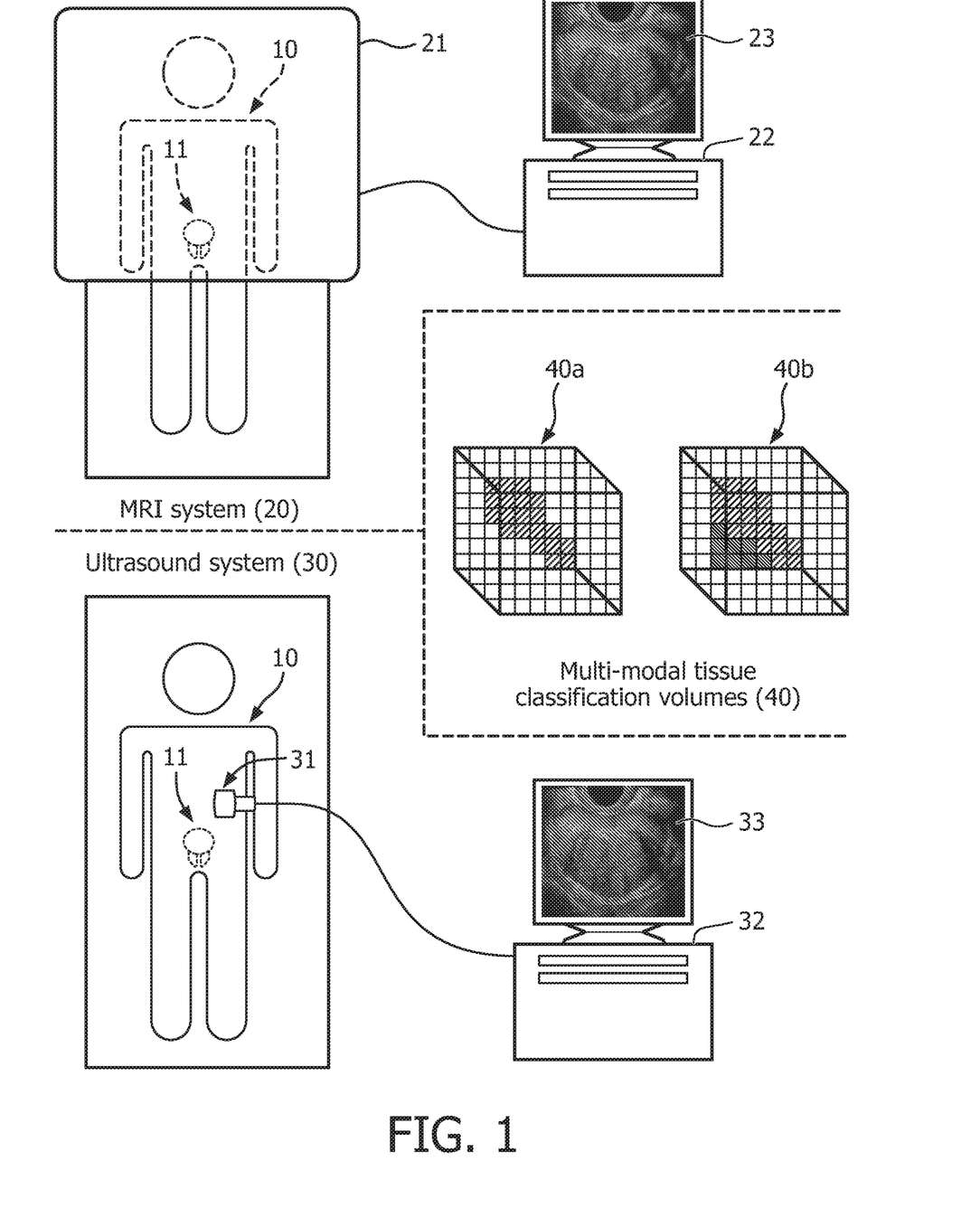
FIG. 1 illustrates multi-modal tissue classification in accordance with the present invention.

Referring to FIG. 1, a MRI system 20 employs a scanner 21 and a workstation 22 to generate a MRI image of an anatomical tissue of a patient, such as, for example, a MRI image 23 of anatomical tissue of a prostate 11 of a patient 10 as shown. In practice, the present invention utilizes one or more MRI systems 20 of various types to acquire MRI features of the anatomical tissue. Examples of types of MRI systems and associated MRI features of an anatomical tissue include, but are not limited to, a $T_2W$ MRI system illustrating normalized intensity-value and/or texture based features of the anatomical tissue, a DWI-MRI system illustrating apparent diffusion coefficient ("ADC") of water in the anatomical tissue, a DCE-MRI system illustrating pharmacokinetic parameters of the anatomical tissue, and MRSI system illustrating metabolic information of the anatomical tissue.

An ultrasound system 30 employs a probe 31 and a workstation 32 to generate an ultrasound image of an anatomical tissue of a patient, such as, for example, a US image 33 of the anatomical tissue of prostate 11 of patient 10 as shown. In practice, the present invention utilizes one or more ultrasound systems 30 of various types to acquire US image features of the anatomical tissue. Examples of types of ultrasound imaging systems 30 and associated US image features of the anatomical tissue include, but are not limited to, a B-mode US imaging system illustrating texture based features of the anatomical tissue and US RF echo imaging system illustrating spectral features of the anatomical tissue.

The present invention performs various known techniques including, but not limited to, image segmentation, image registration, image feature extraction, image delineation and tissue classification, on MRI images and ultrasound images of the anatomical tissue to provide a systematic and objective approach to fuse feature information from the MRI images and the ultrasound images. Specifically, the present invention is premised on combining image features extracted from spatially registered MRI images (e.g., T2W-MRI, DWI-MRI, DCE-MRI and MRSI) and ultrasound images (e.g., a B-mode image and a RF echo image) in order to form a vector of image features for each voxel of a tissue classification volume, such as, for example, tissue classification volume 40a and tissue classification volume 40b as shown in FIG. 1.

In practice, each voxel of a tissue classification volume is classified between a healthy tissue voxel and an unhealthy tissue voxel (e.g., cancerous) based on the image feature vector of the voxel derived from the extracted image features of the spatially registered MRI images and ultrasound images. The quantity and linearity of classifications is not limited by the present invention.

For example, each voxel of tissue classification volume 40a is classified as a being a healthy tissue voxel or an unhealthy tissue voxel (e.g., cancerous) based on the image feature vector of the voxel derived from the extracted image features of the spatially registered MRI images and ultrasound images. As shown in FIG. 1, the healthy tissue voxels are the white voxels and the unhealthy tissue voxels are the black voxels.

By further example, each voxel of tissue classification volume 40b is classified as being either a healthy tissue voxel, an unhealthy tissue voxel (e.g., cancerous) or a borderline unhealthy tissue voxel based on the image feature vector of the voxel derived from the extracted image features of the spatially registered MRI images and ultrasound images. As shown in FIG. 1, the healthy tissue voxels are the white voxels, the unhealthy tissue voxels are the black voxels and the borderline unhealthy tissue voxels are the gray voxels.

Another example, not shown in FIG. 1, is the utilization of a grayscale of voxels ranging from white healthy tissue voxels through multiple gray voxels indicating various probabilities of unhealthiness of corresponding tissue to black unhealthy tissue voxels (e.g., cancerous).

To facilitate an understanding of the present invention, exemplary embodiments of the present invention will now be described herein as directed to a generation of tissue classification volumes of anatomical tissue of a prostate. For purposes of the present invention, the terms "image segmentation", "image (spatial) registration", "image delineation", "image feature extraction", "tissue classification" and "dimensionality reduction" as well as related terms are to be broadly interpreted as known in the art of the present invention. Also, in practice, the present invention applies to any anatomical region (e.g., head, thorax, pelvis, etc.) and to anatomical tissue of any anatomical structure (e.g., organs).

Figure 2:
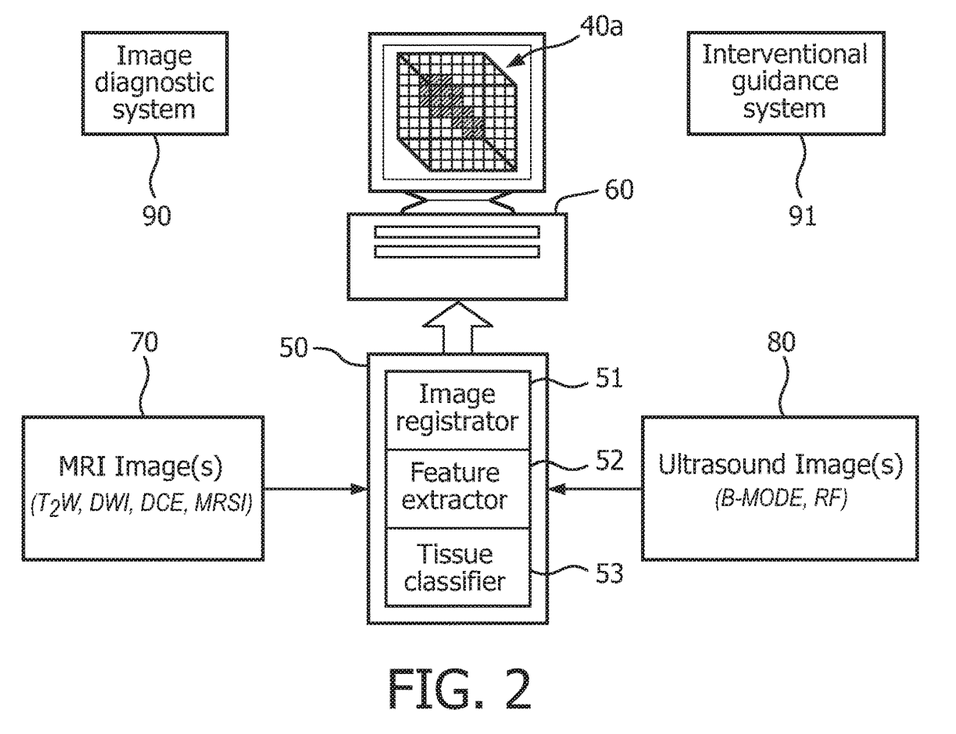
FIG. 2 illustrates an exemplary embodiment of a multi-modal tissue classification workstation in accordance with the present invention.

Referring to FIG. 2, an exemplary workstation 50 employs modules 51-53 for implementing a flowchart 100 (FIG. 3) representative of a multi-modal tissue classification method of the present invention.

In operation, workstation 50 provides a multi-modal data input channel (not shown) for receiving one or more MRI images 70 and one or more US images 80.

Second, image registrator 51 employs technique(s) for spatial registration(s) of the voxels of MRI image(s) 70 and ultrasound image(s) 80.

Third, feature extractor 52 employs technique(s) for extracting image features from the voxels of MRI image(s) 70 and ultrasound image(s) 80.

In practice, as will be further described herein, image registrator 51 and feature extractor 52 operate in tandem to extract image features from the spatially registered voxels of MRI image(s) 70 and ultrasound image(s) 80 for purposes of generating a tissue classification volume having a voxel correspondence with the spatially registered MRI image(s) 70 and ultrasound image(s) 80 and for generating a concatenated n-dimensional image feature vector for each voxel of the tissue classification volume with n equaling a total number of image features.

Fourth, tissue classifier 53 employs technique(s) for classifying, unsupervised or supervised, a tissue type of each voxel of the tissue classification volume as indicated by the image feature vector of each voxel.

Finally, a user interface (not shown) of workstation 50 provides for the display of the tissue classification volume on a voxel-by-voxel basis including zoom and pan capabilities, such as, for example, the display of tissue classification volume 40a as shown in FIG. 2.

In practice, workstation 50 may provide tools for modules 51-53 including, but not limited, to an image segmentation tool to segment voxels of the anatomical tissue from MRI images 70 and US images 80 and an image delineation tool to delineate voxels of MRI images 70 and US images 80 suspicious of being unhealthy (e.g., cancerous).

Also in practice, workstation 50 may be structurally configured in any manner suitable for implementing a multi-modal tissue classification method of the present invention, particularly flowchart 100. In one embodiment, workstation 50 is structurally configured with hardware/circuitry (e.g., processor(s), memory, etc.) for executing modules 51-53 programmed and installed as software/firmware within workstation 50.

Additionally, in practice, workstation 50 may be a stand-alone workstation providing tissue classification volume(s) to an image diagnostic system 90 (e.g., a MRI system or an ultrasound system) for incorporation into a diagnostic procedure as needed and/or an interventional guidance system 91 (e.g., an electromagnetic tracking system, optical tracking system or image tracking system) for incorporation into an interventional procedure as needed. Alternatively, workstation 50 may be incorporated within image diagnostic system 90 or incorporated within interventional guidance system 91.

Figure 3:
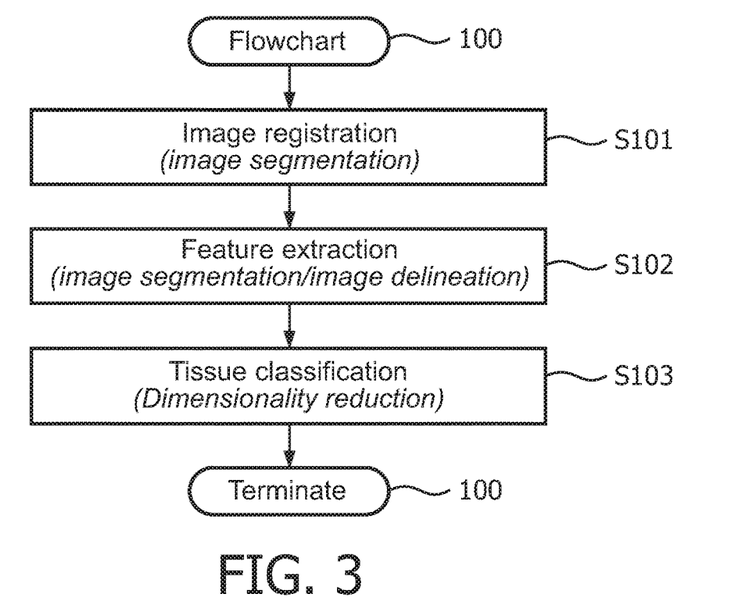
FIG. 3 illustrates a flowchart representative of an exemplary embodiment of a multi-modal tissue classification method in accordance with the present invention.
Figure 4:
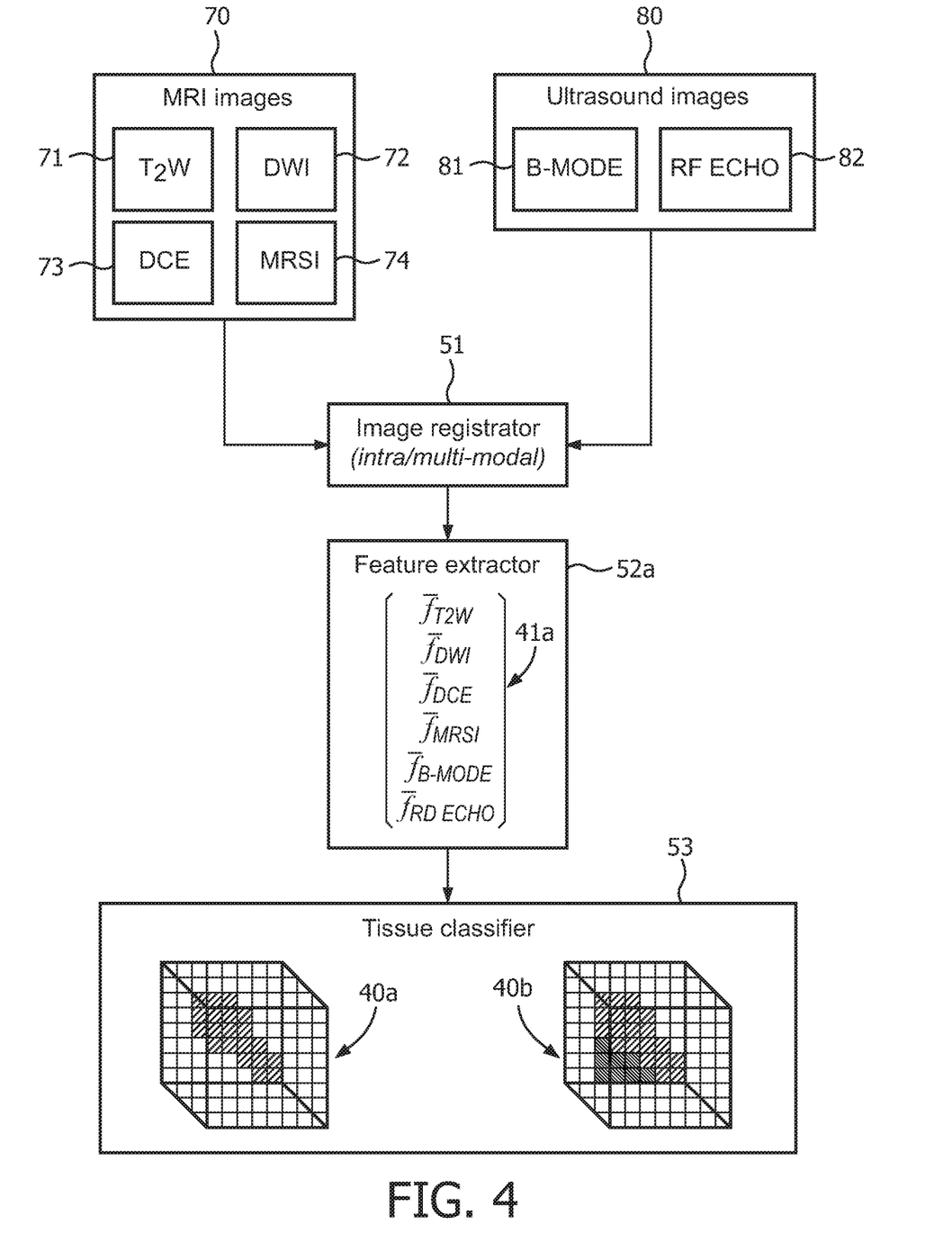
FIG. 4 illustrates a first exemplary implementation of the flowchart illustrated in FIG. 3 by the system illustrated in FIG. 2.
Figure 5:
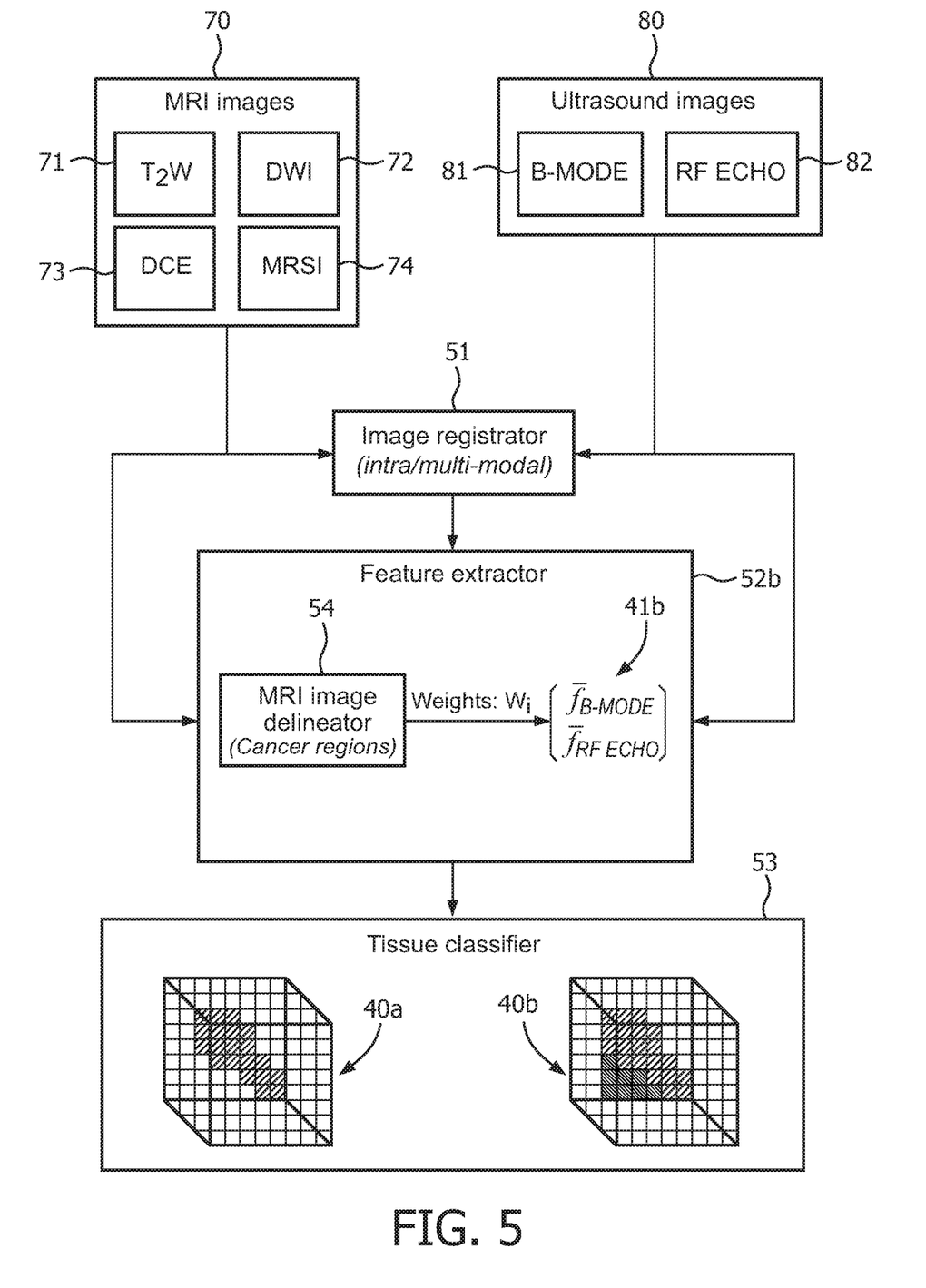
FIG. 5 illustrates a second exemplary implementation of the flowchart illustrated in FIG. 3 by the system illustrated in FIG. 2.

Exemplary executions of flowchart 100 (FIG. 3) by workstation 50 as shown in FIGS. 4 and 5 will now be described herein in the context of MRI images 70 consisting of a $T_2W$ image 71, a DWI image 72, a DCE image 73 and a MRSI image 74, and US images 80 consisting of a B-mode image 81 and a RF echo image 82. From the description, those having ordinary skill in the art will appreciate alternative systems and devices for implementing multi-modal tissue classification methods of the present invention.

Referring to FIG. 3, a stage S101 of flowchart 100 encompasses image registrator 51 performing an intra-modal spatial registration and/or a multi-modal spatial registration for purposes of generating a tissue classification volume having voxel correspondence with the spatially registered images. For example, as shown in FIGS. 4 and 5, image registrator 51 first performs an intra-modal spatial registration of MRI images 70 and then performs a multi-modal spatial registration of MRI images 70 and US images 80 for purposes of generating a tissue classification volume having voxel correspondence with the spatially registered MIR images 70 and US images 80. An image segmentation tool (not shown) may be utilized by image registrator 51 prior to or after the spatial registration(s) to segment voxels of the anatomical tissue (e.g., a prostrate) from MRI images 70 and US images 80.

The resulting spatial registration of MRI images 70 and US images 80 are communicated to feature extractor 52 whereby a stage S102 of flowchart 100 encompasses feature extractor 52 extracting and concatenating image features from each voxel of the spatial registered MRI image(s) 70 and US image(s) 80 to generate a n-dimensional image feature vector for each voxel of the tissue classification volume.

For example, as shown in FIG. 4, a feature extractor 52a extracts normalized intensity-value and/or texture based features of the anatomical tissue from $T_2W$ image 71, an apparent diffusion coefficient ("ADC") of water of the anatomical tissue from DWI image 72, pharmacokinetic parameters of the anatomical tissue from DCE image 73, metabolic information of the anatomical tissue from MRS image 74, texture based image features of the anatomical tissue from B-mode image 81 and spectral image features of the anatomical tissue from RF image 82. From the spatially registered extractions, feature extractor 52a generates a vector 41a, of six (6) dimensional image features for each voxel of the tissue classification volume.

If not utilized by image registrator 51, the image segmentation tool (not shown) may be utilized by feature extractor 52a prior to or after the generation of an image feature vector 41a for each voxel.

By further example, as shown in FIG. 5, a feature extractor 52b utilizes a MRI image delineator 54 to delineate voxels of MRI images 70 representative of unhealthy (e.g., cancerous) portions of the anatomical tissue and generates a weight Wi of a distance from a boundary of the anatomical structure for each voxel from spatially registered MRI images 70. Feature extractor 52b then extracts texture based image features of the anatomical tissue from B-mode image 81 and spectral image features of the anatomical tissue from RF image 82. From the spatially registered extractions, feature extractor 52b generates a weighted vector 41b of two (2) dimensional image features for each voxel of the tissue classification volume.

If not utilized by image registrator 51, the image segmentation tool (not shown) may be utilized by feature extractor 52b prior to or after the generation of an image feature vector 41b for each voxel.

Upon completion of stage S102, the resulting image feature vector for each voxel (e.g., image feature vectors 41a or image feature vectors 41b) of the tissue classification volume is communicated to a tissue classifier 53 whereby a stage S103 of flowchart 100 encompasses tissue classifier 53 classifying, unsupervised or supervised, a tissue type of each voxel for the tissue classification volume (e.g., tissue classification volume 41a and tissue classification volume 41b) as indicated by the image feature vector of each voxel.

For example, all of the image features of the image feature vector of a particular voxel may indicate the associated anatomical tissue is healthy (i.e., normal cells or void of any cellular irregularities). Conversely, one or more of the image features of the image feature vector of a particular voxel may indicate the associated anatomical tissue may be or is unhealthy to some degree (i.e., abnormal cells or inclusive of any cellular irregularity).

Referring to FIG. 2, upon completion of flowchart 100, the tissue classification volume may be displayed by workstation 50, image diagnostic system 90 and/or interventional guidance system 91. Additionally, an overlay or fusion of the tissue classification volume may be displayed on/within an image of the anatomical tissue generated by image diagnostic system 90 and/or interventional guidance system 91.

Referring to FIGS. 1-5, those having ordinary skill in the art will appreciate numerous benefits of the present invention including, but not limited to, an improvement in a sensitivity and specificity of cancer detection for any anatomical tissue (e.g., a prostate). As such, the present invention is applicable in all diagnostic and therapeutic scenarios that would benefit from the ability to localize a location and size of tumors within a gland/section of tissue.

Those having ordinary skill in the art will further appreciate the implementation of the present invention with alternative imaging modalities (e.g., computed tomography and SPECT, PET, etc.).

While various embodiments of the present invention have been illustrated and described, it will be understood by those skilled in the art that the embodiments of the present invention as described herein are illustrative, and various changes and modifications may be made and equivalents may be substituted for elements thereof without departing from the true scope of the present invention. In addition, many modifications may be made to adapt the teachings of the present invention without departing from its central scope. Therefore, it is intended that the present invention not be limited to the particular embodiments disclosed as the best mode contemplated for carrying out the present invention, but that the present invention includes all embodiments falling within the scope of the appended claims.

The invention claimed is:

1. A system for multi-modal tissue classification of an anatomical tissue, the system comprising:
at least one MRI system structurally configured to generate at least one MRI feature of the anatomical tissue;
at least one ultrasound system structurally configured to generate at least one ultrasound image feature of the anatomical tissue; and
a workstation structurally configured to generate a tissue classification volume of the anatomical tissue derived from a spatial registration and an image extraction of the at least one MRI feature and the at least one ultrasound image feature of the anatomical tissue,
wherein the workstation is further structurally configured to classify each voxel of the tissue classification volume as one of a plurality tissue types including at least a healthy tissue voxel and an unhealthy tissue voxel.

2. The system of claim 1, wherein the workstation being structurally configured to generate the tissue classification volume of the anatomical tissue includes:
the workstation structurally configured to spatially register and image extract the at least one MRI feature and the at least one ultrasound image feature of the anatomical tissue; and
the workstation structurally configured to generate an image feature vector for each voxel from the spatial registration and the image extraction of the at least one MRI feature and the at least one ultrasound image feature of the anatomical tissue, each image feature vector including a concatenation of the at least one MRI feature and the at least one ultrasound image feature of the anatomical tissue associated with a corresponding voxel.

3. The system of claim 2, wherein the workstation being structurally configured to classify each voxel of the tissue classification volume as one of the plurality tissue types including at least the healthy tissue voxel and the unhealthy tissue voxel includes:
the workstation structurally configured to derive the classification of each voxel of the tissue classification volume as one of the tissue types from the concatenation of the at least one MRI feature and the at least one ultrasound image feature of the anatomical tissue included within a corresponding image feature vector.

4. The system of claim 1, wherein the workstation being structurally configured to generate the tissue classification volume of the anatomical tissue includes:
the workstation structurally configured to image extract at least two ultrasound image features of the anatomical tissue; and
the workstation structurally configured to generate an image feature vector for each voxel from the image extraction of the at least two ultrasound image features of the anatomical tissue, each image feature vector including a concatenation of the at least two ultrasound image features of the anatomical tissue associated with a corresponding voxel.

5. The system of claim 4, wherein the workstation being structurally configured to generate the tissue classification volume of the anatomical tissue includes:
the workstation structurally configured to spatially register the at least one MRI feature and the at least two ultrasound image features;
the workstation structurally configured to generate a weighted factor for each voxel from the spatial registration of the at least one MRI feature and the at least two ultrasound image features, each weighted factor being derived from a delineation of each at least one MRI feature of the anatomical tissue representative of an unhealthy portion of the anatomical tissue; and
the workstation structurally configured to apply each weighted factor to the at least two ultrasound image features.

6. The system of claim 5, wherein the workstation being structurally configured to classify each voxel of the tissue classification volume as one of the plurality tissue types including at least the healthy tissue voxel and the unhealthy tissue voxel:
the workstation structurally configured to derive the classification of each voxel of the tissue classification volume as one of the tissue types from the concatenation of the at least two ultrasound image features.

7. The system of claim 1, wherein the plurality of tissue types further includes a borderline unhealthy tissue voxel between the healthy tissue voxel and the unhealthy tissue voxel.

8. The system of claim 1, wherein the plurality of tissue types further includes a plurality of probable unhealthy tissue voxels ranging between the healthy tissue voxel and the unhealthy tissue voxel.

9. The system of claim 1, further comprising:
an image diagnostic system structurally configured to incorporate the tissue classification volume into a diagnostic procedure.

10. The system of claim 1, further comprising:
an interventional guidance system structurally configured to incorporate the tissue classification volume into an interventional procedure.

11. A workstation, comprising:
at least one processor and a non-transitory machine-readable storage memory encoded with modules for execution by the at least one processor for a multi-modal tissue classification of an anatomical tissue, the modules including:
an image registrator and a feature extractor structurally configured to generate a tissue classification volume of the anatomical tissue derived from a spatial registration and an image extraction of at least one MRI feature of the anatomical tissue and at least one ultrasound image feature of the anatomical tissue; and
a tissue classifier structurally configured to classify each voxel of the tissue classification volume as one of a plurality tissue types including at least a healthy tissue voxel and an unhealthy tissue voxel.

12. The workstation of claim 11, wherein the image registrator and the feature extractor structurally configured to generate the tissue classification volume of the anatomical tissue includes:
   the image registrator structurally configured to spatially register the at least one MRI feature and the at least one ultrasound image feature of the anatomical tissue;
   the feature extractor structurally configured to image extract a spatially registered at least one MRI feature and at least one ultrasound image feature of the anatomical tissue; and
   the feature extractor structurally configured to generate an image feature vector for each voxel from the image extraction of the spatially registered at least one MRI feature and at least one ultrasound image feature of the anatomical tissue, each image feature vector including a concatenation of the at least one MRI feature and at least one ultrasound image feature of the anatomical tissue associated with a corresponding voxel.

13. The system of claim 12, wherein the tissue classifier structurally configured to classify each voxel of the tissue classification volume as one of the tissue types including at least the healthy tissue voxel and the unhealthy tissue voxel includes:
   the tissue classifier structurally configured to derive a classification of each voxel of the tissue classification volume as one of the tissue types from the concatenation of the at least one MRI feature and the at least one ultrasound image feature of the anatomical tissue included within a corresponding image feature vector.

14. The workstation of claim 11, wherein the image registrator and the feature extractor structurally configured to generate the tissue classification volume of the anatomical tissue includes:
   the image registrator structurally configured to spatially register the at least one MRI feature and at least two ultrasound image features of the anatomical tissue;
   the feature extractor structurally configured to image extract the at least two ultrasound image features of the anatomical tissue;
   the feature extractor further structurally configured to generate an image feature vector for each voxel from the image extraction of the at least two ultrasound image features of the anatomical tissue, each image feature vector including a concatenation of the at least two ultrasound image features of the anatomical tissue associated with a corresponding voxel;
   the feature extractor further structurally configured to generate a weighted factor for each voxel from the spatial registration of the at least one MRI feature of the anatomical tissue, each weighted factor being derived from a delineation of the at least one MRI feature of the anatomical tissue representative of a suspicious unhealthy portion of the anatomical tissue; and
   the feature extractor further structurally configured to apply each weighted factor to each image feature vector of the corresponding voxel.

15. The workstation of claim 14, wherein the tissue classifier being structurally configured to classify each voxel of the tissue classification volume as one of the tissue types including at least the healthy tissue voxel and the unhealthy tissue voxel includes:
   the tissue classifier structurally configured to derive the classification of each voxel of the tissue classification volume as one of the tissue types from the concatenation of the at least one MRI feature and at least two ultrasound image features of the anatomical tissue of the anatomical tissue included within a corresponding image feature vector.

* * * * *